(12) United States Patent
Kirby et al.

(10) Patent No.: US 6,911,576 B1
(45) Date of Patent: Jun. 28, 2005

(54) TRANSGENIC POPLAR TREES COMPRISING GLUTAMINE SYNTHETASE FROM PINE HAVING IMPROVED NITROGEN METABOLISM AND METHODS OF MAKING AND USING THE SAME

(75) Inventors: Edward G. Kirby, Basking Ridge, NJ (US); Francisco Canovas Ramos, AlhAurin de la Torre (ES); Fernardo Gallardo Alba, Benalmadena (ES)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/763,005

(22) PCT Filed: Aug. 11, 1999

(86) PCT No.: PCT/US99/18267

§ 371 (c)(1),
(2), (4) Date: Apr. 20, 2001

(87) PCT Pub. No.: WO00/09726

PCT Pub. Date: Feb. 24, 2000

Related U.S. Application Data

(60) Provisional application No. 60/096,032, filed on Aug. 11, 1998.

(51) Int. Cl.[7] ............................. A01H 5/00; A01H 5/10; C12N 9/00; C12N 15/82; C12N 15/84
(52) U.S. Cl. ...................... 800/290; 800/278; 800/294; 800/295; 800/298; 536/23.1; 536/23.2; 536/23.6; 435/320.1; 435/419
(58) Field of Search ................................. 800/290, 295, 800/298, 294, 278; 536/23.1, 23.2, 23.6; 435/320.1, 468, 69.1, 419; 530/370

(56) References Cited

U.S. PATENT DOCUMENTS 5,955,651 A * 9/1999 Coruzzi ...................... 800/298

FOREIGN PATENT DOCUMENTS

EP  0303780  * 5/1988

OTHER PUBLICATIONS

Feuillet et al., Tissue–and cell–specific expression of a cinnamyl alcohol dehydrogenase promoter in transgenic poplar plants. 1995, Plant Molecular Biology, vol. 27, pp. 651–667.*
Canton et al., Molecular charaterization of a cDNA clone encoding glutamine synthetase from a gymnosperm, *Pinus sylvestris*. 1993, Plant Molecular Biology, vol. 22, pp. 819–828.*
van Engelen et al., pBINPLUS: an improved plant transformation vector based on pBIN19. 1995. Transgenic Research, vol. 4, pp. 288–290.*
Noir et al., Origin, diversity and evolution of NBS–type disease–resistance gene homologues in coffee tree (*Coffea L*). 2001. Mol Genet Genomics, vol. 265, pp. 654–662.*
Genbannk Accession No. X69822.*
Fourgoux–Nicol et al., 1999, Plant Molecular Biology, vol. 40 :857–872.*

* cited by examiner

*Primary Examiner*—Amy J. Nelson
*Assistant Examiner*—Russell Kallis
(74) *Attorney, Agent, or Firm*—Dann, Dorfman, Herrell & Skillman

(57) ABSTRACT

Nitrogen is one of the principal factors limiting vegetative production. The present invention has improved the nitrogen metabolism in Poplar by integrating a transgene constitutively expressing a pine glutamine synthetase into the plan genome. The resulting transgenic trees exhibit higher growth rates, protein and chlorophyll contents, and leaf area than equivalent untransformed trees. It is contemplated that this approach to nitrogen improvement will be equally successful for all woody perennials. Provided with the invention is an expression casette, a vector, and a method for increase glutamine synthetase activity in woody perennials, as well as transgenic woody perennials with enhanced nitrogen metabolism and accompanying phenotype.

12 Claims, 3 Drawing Sheets

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
tgttgatgcc cattataagg cttgtctcta           30

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
ggtcgtctca gcaatcat                        18

<210> SEQ ID NO 3
<211> LENGTH: 1423
<212> TYPE: DNA
<213> ORGANISM: Pinus sylvestris

<400> SEQUENCE: 3
ttcccttcct ctggtttgtt ttggagagtg gccatgtcga gcgtattaac agaccttctc     60
aaccttgacc tgagcgacgt gacagagaag gtcattgcag agtatatatg gattggagga    120
tcaggaatgg atatgcgcag taaagccaga tctctgtcag gacctgtgag tagcgttaaa    180
gagcttccca aatggaacta tgacggctcc agcactggac aggctcaagg acatgacagc    240
gaagtcattc tatatccaca agctatcttc cgtgatccat ttcgcagagg aaagcacatt    300
ttggtaatct gtgatgccta ctctcctaat gggactgcta ttccttccaa caagagggct    360
gcagcagcga aaattttaa cgaaaaggcg gttagtgatg aagagacatg gtacgggctt    420
gaacaagaat atacactgtt gcaaaaggac gtcaaatggc ctcttggctg gccaattggt    480
ggctaccccg gtcctcaggg cccatattac tgtggagttg gagctgacaa agcctgggga    540
cgagacattg ttgatgccca ttataaggct tgtctctatt caggaatcaa tatcagtggc    600
atcaatggag aagtcatgcc agggcagtgg gaatttcaag taggtccgtc agtgggtatc    660
tcagcagcag atgagctgtg gtgtgctcgt tttattatgg agaggattac agaaaaggcg    720
ggtgtcgttc tgtcctttga tcccaagcca attgaggggg actggaatgg tgctggatgc    780
cacacaaatt acagcaccaa gtccatgcgc aaggagggag gcttcgaagt aattaagaaa    840
gcaatagaaa aactgaagtt gaggcataag gagcatattt ctgcctatgg ggagggaaat    900
gagagacgcc tcactggtcg gcacgagaca gcagacatga ataccttttc ctgggtgtt    960 gcaaatcgag gagcttcagt tagagtgggc cgggacacag aaaaagaagg aaaaggttat   1020
tttgaggacc gtcgacctgc ttcaaacatg gatccataca tagtgacttc tatgattgct   1080
gagacgacca ttctatggaa accttaaatt acaaagtgga ggccagttac acgcgtggtc   1140
gtggtgcttt gctttggagg ccagcgtcac tgataagcta atatgtatgt aaatgtgatg   1200
ccaatgttta agtaggttgg taactttgct ttggttgtgg gtagacctga actttggtca   1260

```
aacaatttcc tcttgctata tggatatata tatattttg  tatttgttct acttgtaata   1320
tggcgagggc tttaaaagac tctcttttac ctttatttat tccgttgtgg aagatgtatt   1380
cgacaaattg tttagaatgt ttgaatatga tatattcttt gtg                    1423
```

<210> SEQ ID NO 4
<211> LENGTH: 357
<212> TYPE: PRT
<213> ORGANISM: Pinus sylvestris

<400> SEQUENCE: 4

```
Met Ser Ser Val Leu Thr Asp Leu Leu Asn Leu Asp Leu Ser Asp Val
 1               5                  10                  15

Thr Glu Lys Val Ile Ala Glu Tyr Ile Trp Ile Gly Gly Ser Gly Met
                20                  25                  30

Asp Met Arg Ser Lys Ala Arg Ser Leu Ser Gly Pro Val Ser Ser Val
            35                  40                  45

Lys Glu Leu Pro Lys Trp Asn Tyr Asp Gly Ser Thr Gly Gln Ala
        50                  55                  60

Gln Gly His Asp Ser Glu Val Ile Leu Tyr Pro Gln Ala Ile Phe Arg
 65                  70                  75                  80

Asp Pro Phe Arg Arg Gly Lys His Ile Leu Val Ile Cys Asp Ala Tyr
                 85                  90                  95

Ser Pro Asn Gly Thr Ala Ile Pro Ser Asn Lys Arg Ala Ala Ala Ala
            100                 105                 110

Lys Ile Phe Asn Glu Lys Ala Val Ser Asp Glu Glu Thr Trp Tyr Gly
        115                 120                 125

Leu Glu Gln Glu Tyr Thr Leu Leu Gln Lys Asp Val Lys Trp Pro Leu
130                 135                 140

Gly Trp Pro Ile Gly Gly Tyr Pro Gly Pro Gln Gly Pro Tyr Tyr Cys
145                 150                 155                 160

Gly Val Gly Ala Asp Lys Ala Trp Gly Arg Asp Ile Val Asp Ala His
                165                 170                 175

Tyr Lys Ala Cys Leu Tyr Ser Gly Ile Asn Ile Ser Gly Ile Asn Gly
            180                 185                 190

Glu Val Met Pro Gly Gln Trp Glu Phe Gln Val Gly Pro Ser Val Gly
        195                 200                 205

Ile Ser Ala Ala Asp Glu Leu Trp Cys Ala Arg Phe Ile Met Glu Arg
210                 215                 220

Ile Thr Glu Lys Ala Gly Val Val Leu Ser Phe Asp Pro Lys Pro Ile
225                 230                 235                 240

Glu Gly Asp Trp Asn Gly Ala Gly Cys His Thr Asn Tyr Ser Thr Lys
                245                 250                 255

Ser Met Arg Lys Glu Gly Gly Phe Glu Val Ile Lys Lys Ala Ile Glu
            260                 265                 270

Lys Leu Lys Leu Arg His Lys Glu His Ile Ser Ala Tyr Gly Glu Gly
        275                 280                 285

Asn Glu Arg Arg Leu Thr Gly Arg His Glu Thr Ala Asp Met Asn Thr
    290                 295                 300

Phe Ser Trp Gly Val Ala Asn Arg Gly Ala Ser Val Arg Val Gly Arg
305                 310                 315                 320

Asp Thr Glu Lys Glu Gly Lys Gly Tyr Phe Glu Asp Arg Arg Pro Ala
                325                 330                 335
```

```
-continued

Ser Asn Met Asp Pro Tyr Ile Val Thr Ser Met Ile Ala Glu Thr Thr
            340             345             350

Ile Leu Trp Lys Pro
        355
```

TRANSGENIC POPLAR TREES COMPRISING GLUTAMINE SYNTHETASE FROM PINE HAVING IMPROVED NITROGEN METABOLISM AND METHODS OF MAKING AND USING THE SAME

This application is a §371 Application of PCT/US99/18267, filed Aug. 11, 1999 which in turn claims priority to U.S. Provisional Application No. 60/096,032, filed Aug. 11, 1998.

FIELD OF THE INVENTION

This invention relates to the field of plant breeding, forestry, plant transformation, and mineral nutrition. More specifically, a transgenic woody perennial plant is provided, having improved nitrogen metabolism.

BACKGROUND OF THE INVENTION

Various scientific and scholarly articles are referred to in brackets throughout the specification. These articles are incorporated by reference herein to describe the state of the art to which this invention pertains.

Plant growth and biomass accumulation are dependent on the availability, absorption and assimilation of nutrients from the environment. Nitrogen is one of the principal factors limiting vegetative production. Only a few microorganisms are capable of reducing molecular atmospheric nitrogen ($N_2$) to a form usable by the plant. Plants themselves are unable to do this. Although some plants can utilize $N_2$ through a symbiosis with certain nitrogen-reducing micro-organisms, the majority of plants obtain nitrogen by assimilating nitrate and ammonium from the soil.

In forest trees, the capacity to assimilate nitrogen is of particular significance. In communities of perennial, long-lived species, most of the nitrogen is fixed in living tissue and is not in the soil. The availability of inorganic nitrogen in the soil is a limiting factor to tree growth (Cole and Rapp, 1981, In Reiche DE (ed) *Dynamic Properties of Forest Ecosystem*, pp. 341–409, Cambridge University Press, Cambridge). Poplar trees are often used in reforestation efforts, and a variety that can grow well in low nitrogen soil would be very useful. Additionally, fast-growing, high biomase poplar trees are also very valuable for fodder and industrial wood production.

Assimilation of nitrogen by plants entails the reduction of nitrate to ammonium and its incorporation into carbon skeletons. Ammonium is assimilated into organic nitrogen mainly through the reaction catalyzed by glutamine synthetase (GS; EC 6.3.1.2). The amide group from the product of the GS reaction, glutamine, is then transferred to glutamate by action of glutamate synthetase (GOGAT; EC 1.4.7.1 and 1.4.1.14). This metabolic pathway is of crucial importance, since glutamine and glutamate are the donors for the biosynthesis of major nitrogen-containing compounds, including amino acids, nucleotides, chlorophylls, polyamines, and alkaloids (Miflin and Lea, 1980, In Miflin B J (ed) *The Biochemistry of Plants* Vol 5 pp. 169–202, Academic Press Inc., London).

The biochemistry and molecular biology of the GS/GOGAT cycle has been extensively studied due to the key role these enzymes play in plant growth and development (Crawford and Arst, 1993, Ann Rev Genet 27:115–146; Lam et al., 1996, Ann Rev Plant Physiol Plant Mol Biol 47: 569–593). GS is encoded by a small family of homologous nuclear genes. The enzyme is represented by two main isoenzymes: GS is localized in the cytosal and GS2 is a chloroplastic enzyme. Octameric GS holoenzymes also differ in their subunit compositions, GS1 is comprised of polypeptides of 38–41 kD in most plant species, whereas the size of GS2 subunit polypeptides is about 45 kD.

The physiological roles of GS1 and GS2 are now relatively well-established in angiosperms (Lea, 1997, In Dey P M, Harborne J B (eds) *Plant Biochemistry*, pp. 273–313, Academic Press, San Diego). In leaves, GS2 is expressed in photosynthetic tissues and is responsible for the incorcoration of ammonium from nitrate assimilation and photorespiration. GS1 as mainly expressed in vascular elements and functions to generate glutamine for nitrogen transport within the plant.

Approaches to modify levels of key enzymes involved in steps in carbon and nitrogen assimilation and primary metabolism have been considered as a means to improve vegetative growth and biomass production (Foyer and Ferrario, 1994, Biochem Soc Trans 22: 909–915, and the references therein). All the work on metabolic engineering of the nitrogen assimilation using transgeric plants has been done in annual, *herbaceous* species (e.g., tobacco, *Lotus corniculatus* L.). Increases in protein content and biomass production have been reported in transgenic tobacco expressing a pea GS1 gene (Coruzzi, 1995, International Application, Patent Cooperation Treaty, WO 95/09911).

However, success with constitutively-expressed GS transgenes has been unpredictable. In other reports, transgenic herbaceous plants which over-express cytosolic GS1 fail to exhibit changes in protein, chlorophyll or biomass production (Eckes et al., 1989, Mol Gen Genet 217: 263–268; Hirel et al., 1992, Plant Mol Biol 20: 207–218; Temple et al., 1993, Mol Gen Genet 236: 315–325). These discrepancies may be due to the instability of the holoenzyme in a heterologous system and/or to the different plant species used in the transformation studies.

The effects of GS over-expression may be unique in the woody perennial species, as compared to herbaceous annual species. Woody perennial species uniquely store assimilated nitrogen during periods of less favorable growth conditions, such as would occur in winter. In poplar, for example, assimilated nitrogen can reside as vegetative storage proteins (VSPs). VSPs can be mobilized to support development during active growth (Ryan and Bormann, 1982, BioScience 32: 29–32). Synthesis of seasonal VSPs in poplar is dependent on environmental factors, including photoperiod and nitrogen availability (reviewed in Coleman, 1993, in YWC N. B. Klopfenstein M-S. Kim, M. R. Ahuja, eds, *Micropropagation, Genetic Engineering, and Molecular Biology of Populus*, Gen. Tech. Rep. RM-GTR-297, pp 124–130, Rocky Mountain Forest and Range Experiment Station, Fort Collins). Since spring shoot growth in poplar is correlated with nitrogen recycling (Coleman et al., 1993, Plant Physiol 102: 53–59) and glutamine is the main amino acid transported in spring xylem sap (Sauter and van Cleve, 1992, Trees 7: 26–32), enhancement of nitrogen-use efficiency as a result of ectopic GS expression could affect the availability of reduced nitrogen for initiation of rapid spring growth.

The slow growth of woody perennials as compared to herbaceous annuals may also make the effect of GS over-expression on plant growth and physiology unpredictable. Because of this comparatively slow growth rate, a particular enzyme or metabolic pathway may influence plant growth and development may be quite different than that of fast-growing herbaceous plants. This may be especially true when targets for metabolic engineering are enzymes involved in assimilation and primary metabolism, therefore having wide-spread effects on plant development.

SUMMARY OF THE INVENTION

The present invention relates to the production of transgenic woody perennial plants having improved nitrogen metabolism due to expression of chimeric transgenes, comprising the coding sequence of glutamine synthetase operably linked to appropriate 5' and 3' regulatory sequences. The present invention particularly relates to altering the expression of glutamine synthetase in such plants, thereby improving numerous agronomic, economical and environmental features of the plants, such as their ability to grow on nitrogen-poor soil, or grow optimally with minimal additions of fertilizer. Other improvements found in these transgenic plants include enhanced or novel phenotypes, such as faster growth, higher biomass production, and higher nutritional quality of fruit, seeds and foliage.

One aspect of the invention is a plant expression cassette that will alter the level and location of glutamine synthetase in plants. This expression cassette comprises a glutamine synthetase gene operably linked to a promoter. In preferred embodiments, the glutamine synthetase gene is from a gymnosperm, the genus *Pinus*, and the species *Pinus sylvestris*. In other preferred embodiments, the expression cassette additionally comprises the cauliflower mosaic virus 35S promoter and the NOS terminator. In other preferred embodiments, the expression cassette comprises a sequence that is at least 70% identical to Genbank Accession No. X69822 (SEQ ID NO: 3), encodes a protein that is at least 70% similar to the protein sequence encoded by Genbank Accession No. X69822 (SEQ ID NO: 4), hybridized to Genbank Accession No. X69822 (SEQ ID NO: 3) at moderate stringency, or is Genbank Accession No. X69822 (SEQ ID NO: 3).

Another aspect of the invention is a vector containing the expression cassette. In preferred embodiments, the vector is an *Agrobacterium* binary vector and pBIN19. In another preferred embodiment, the vector comprises the neomycin phosphotransferase II coding sequence.

Another aspect of the invention is a method for producing a transgenic plant with improved nitrogen metabolism by transforming a plant in vitro with the aforementioned expression cassette. In preferred embodiments, the plant is a woody perennial, in the family Salicaceae, in the genus *Populus*, a hybrid *Populus tremula* X *P. alba*, and clone INRA 717 1-B4 of the hybrid *Populus tremula* X *P. alba*. In other preferred embodiments, the method uses *Agrobacterium tumefaciens* and the *Agrobacterium* binary vector containing the glutamine synthetase expression cassette. This aspect includes a trarsgenic plant made by the method and a reproductive unit from the plant.

Another aspect of the invention is a transgenic woody perennial plant with improved nitrogen metabloism which comprises at least one transgene expressing the coding sequence of glutamine synthetase. In preferred embodiments, the glutamine synthetase gene is from a gymnosperm, from *Pinus sylvestris*, and is Genbank Accession No. X69822. In other preferred embodiments, the transgenic plant is in the family Salicaceae, the genus *Populus*, is a hybrid *Populus tremula* X *P. alba*, and is clone INRA 717 1-B4 of the hybrid *Populus tremula* X *P. alba*. This aspect additionally includes a reproductive unit from the transgenic plant.

Another aspect of the invention is a transgenic woody perennial that exhibits a growth rate over the first three months in the greenhouse that is at least 10% greater than that of equivalent untransformed plants. In a preferred embodiment, the plant additionally exhibits a protein concentration (g/gfw) that is at least 10% greater than that of equivalent untransformed plants after the first 3 months in the greenhouse. In a most preferred embodiment, the transgenic plant additionally exhibits a chlorophyll concentration (g/gfw) that is at least 10% greater than that of equivalent untransformed plants after the first 3 months in the greenhouse. In other preferred embodiments, the plant is in the family Salicaceae, in the genus *Populus*, a hybrid of *Populus tremula* X *P. alba*, and is clone INRA 717 1-B4 of the hybrid *Populus tremula* X *P. alba*. This aspect additionally contains a reproductive unit of the transgenic plant.

Another aspect of the invention is a transgenic woody perennial plant with improved nitrogen metabloism which comprises at least one transgene expressing the coding sequence of glutamine synthetase. In preferred embodiments, the glutamine synthetase gene is from a gymnosperm, from *Pinus sylvestris*, and is Genbank Accession No. X69822 (SEQ ID NO:3). In other preferred embodiments, the transgenic plant is in the family Salicaceae, the genus *Populus*, is a hybrid *Populus tremula* X *P. alba*, and is clone INRA 717 1-B4 of the hybrid *Populus tremula* X *P. alba*. This aspect additionally includes a reproductive unit from the transgenic plant.

Another aspect of the invention is a transgenic woody perennial that exhibits a growth rate over the first two months in the greenhouse that is at least 10% greater than that of equivalent untransformed plants. In a preferred embodiment, the plant additionally exhibits a protein concentration (g/gfw) that is at least 10% greater than that of equivalent untransformed plants after the first 3 months in the greenhouse. In a most preferred embodiment, the transgenic plant additionally exhibits a chlorophyll concentration (g/gfw) that is at least 10% greater than that of equivalent untransformed plants after the first 3 months in the greenhouse. In other preferred embodiments, the plant is in the family Salicaceae, in the genus *Populus*, a hybrid of *Populus tremula* X *P. alba*, and is clone INRA 717 1-B4 of the hybrid *Populus tremula* X *P. alba*. This aspect additionally contains a reproductive unit of the transgenic plant.

DETAILED DESCRIPTION OF THE INVENTION

I. Definitions

Figure 1:
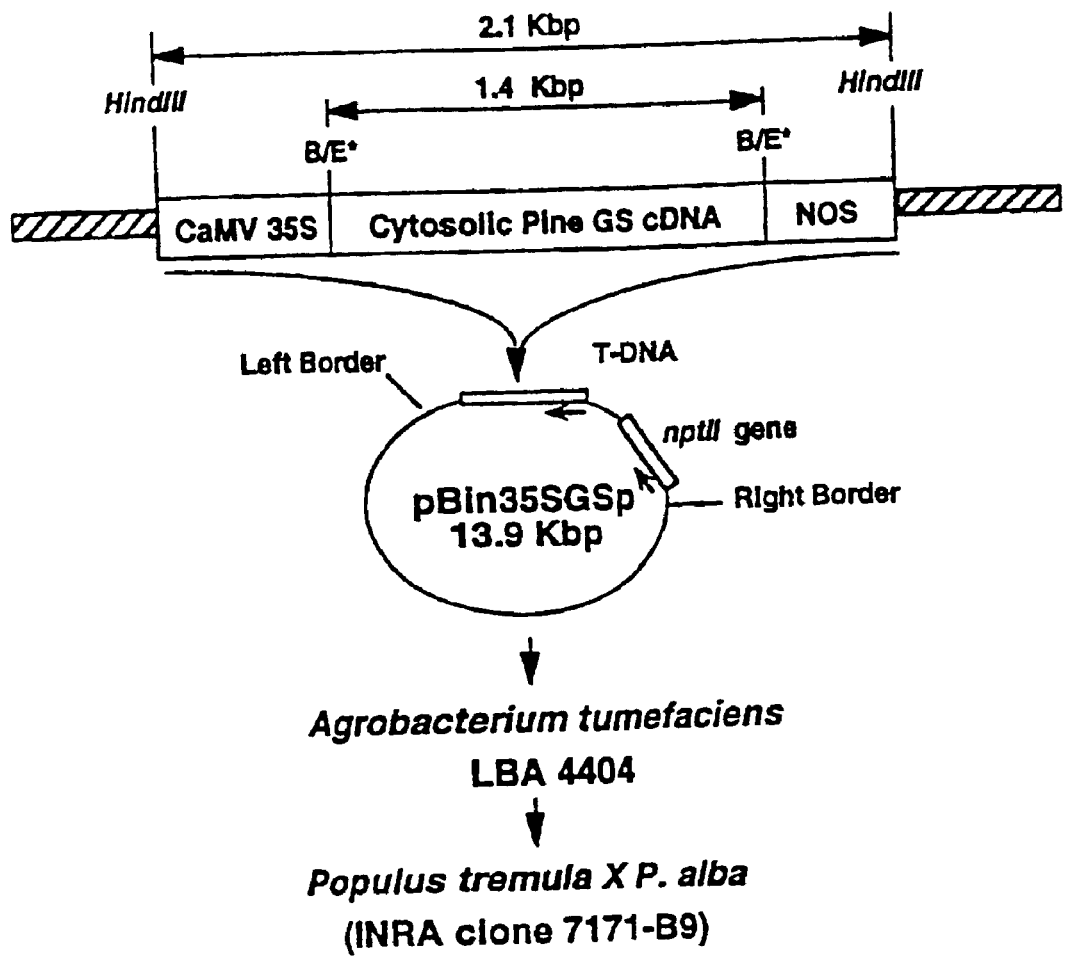
FIG. 1. Strategy for transformation of hybrid poplar (*Populus tremula* X *P. alba* [INRA 717 1-B] with *Agrobacterium tumefaciens* (LBA 4404) containing the binary vector pBin35SGSp. B/E* represents a blunt-ended BamHI/EcoRI site. The arrows in pBin35SGSp indicate the sense of transcription of CaMV 35S-GS-NOS and nptII genes.

Various terms relating to the methods and compositions of the present invention are used hereinabove and also throughout the specifications and claims.

Various terms relating to the biological molecules of the present invention are used hereinabove and also throughout the specifications and claims. The terms "substantially the same," "percent similarity" and "percent identity" are defined in detail below.

With reference to nucleic acids of the invention, the term "isolated nucleic acid" is sometimes used. This term, when applied to genomic DNA, refers to a DNA molecule that is separated from sequences with which it is immediately contiguous (in the 5' and 3' directions) in the naturally occurring gencme of the organism from which it was derived. For example, the "isolated nucleic acid" ray comprise a DNA molecule inserted into a vector, such as a plasmid or virus vector, or integrated into the genomic DNA of a prokaryote or eukaryote. An "isolated nucleic acid molecule" may also comprise a cDNA molecule or a synthetic DNA molecule.

With respect to RNA molecules of the invention, the term "isolated nucleic acid" primarily refers to an RNA molecule enccded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

Nucleic acid sequences and amino acid sequences can be compared using computer programs that align the similar sequences of the nucleic or amino acids thus define the differences. For purposes of this invention, the GCG Wisconsin Package version 9.1, available from the Genetics Computer Croup in Madison, Wis., and the default parameters used (gap creation penalty=12, gap extension penalty=4) by that program are the parameters intended to be used herein to compare sequence identity and similarity.

The term "substantially the same" refers to nucleic acid or amino acid sequences having sequence variations that do not materially affect the nature of the protein (i.e. the structure, thermostability characteristics and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantialiy the same" refers generally to conservative substitutions and/or variations in regions of the polypeptide not involved in determination of structure or function.

The terms "percent identical" and "percert similar" are also used herein in comparisons among amino acid and nucleic acid sequences. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

The term "ectopic expression" refers to a pattern of subcellular, cell-type, tissue-type and/or developmental or temporal (e.g., light/dark) expression that is not normal for the particular gene or enzyme in question. Such ectopic expression does not necessarily exclude expression in normal tissues or developmental stages.

The term "overexpression" means a greater than normal expression level of a gene in the particular tissue, cell and/cor developmental or temporal stage for the gene. Such overexpression results in "overproduction" of the enzyme encoded by the gene, which means a greater than normal production of the enzyme in a particular tissue or cell, or developmental or temporal stage for the enzyme. The terms "underexpression" and "underproduction" have an analogously converse meaning, and are used interchangeably with the term "suppression".

In regards to the present invention, "equivalent plants" are ones of the same genotype or cultivar, at the same age, and having been grown under the same conditions. In the case where one is a transgenic plant, the equivalent plant may be transformed by a similar DNA construct but without the glutamine synthetase transgene, or may not be transformed but regenerated from tissue culture.

In this invention, the term "promoter" or "promoter region" refers to the 5' regulatory regions of a gene, including promoters per se (e.g., CaMV 35S promoters and/or tetracycline repressor/operator gene promoters), as well as other transcriptional and translational regulatory sequences.

The term "selectable marker" refers to a gene product that confers a selectable phenotype, such as antibiotic resistance, on a transformed cell or plant. Selectable markers are encoded by expressible DNA sequences, which are sometimes referred to herein as "selectable marker genes."

The terms "operably linked", "operably inserted" or "operably associated" mean that the regulatory sequences necessary for expression of the coding sequences are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The erm "DNA construct" refers to genetic sequence used to transform plant cells and generate progeny transgenic plants. At minimum a DNA construct comprises a coding region for a selected gene product, operably linked to 5' and 3' regulatory sequences for expression in transformed plants. In preferred embodiments, such constructs are chimeric, i.e., the coding sequence is from a different source one or more of the regulatory sequences (e.g., coding sequence from tobacco and promoter from cauliflower mosaic virus). However, non-chimeric DNA constructs also can be used.

DNA constructs may be administered to plants in a viral or plasmid vector. Other methods of delivery such as *Agrobacterium* T-DNA mediated transformation and transformation using the biolistic process are also contemplated to be within the scope of the present invention. The transforming DNA may be prepared according to standard protocols such as those set forth in Ausubel et al. (1998). A plant species or cultivar may be transformed with a DNA construct (chimeric or non-chimeric) that encodes a polypeptide from a different plant species or cultivar (e.g., poplar transformed with a gene encoding a pine protein). Alternatively, a plant species or cultivar may be transformed with a DNA construct (chimeric or non-chimeric) that encodes a polypeptide from the same plant species or cultivar. The term "transgene" is sometimes used to refer to the DNA construct within the transformed cell or plant.

In accordance with the present invention, nucleic acids having the appropriate sequence homology with the nucleic acids of the invention may be identified by using hybridization and washing conditions of appropriate stringency. For example, hybridizations may be performed, according to the method of Sambrook et al. (1989, *Molecular Cloning*, Cold Spring Harbor Laboratory), using a hybridization solution comprising: 5×SSC, 5× Denhardt's reagent, 1.0% SDS, 100 μg/ml denatured, fragmented saimon sperm DNA, 0.05% sodium pyrophosphate and up to 50% formamide. Hybridization is carried out at 37–42° C. for at least six hours. Following hybridization, filters are washec as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology (Sambrook et al., 1989, supra):

$$T_m = 81.5° C. + 16.6 \text{ Log}[Na+] + 0.41(\% G+C) - 0.63(\% \text{ formamide}) - 600/\#bp \text{in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1–1.50° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20–25° C. below the calculated $T_m$ of the hybrid. Wash conditions should be as stringent as possible for the degree of identity of the probe for the target. In general, wash conditions are selected to be approximately 12–20° C. below the $T_m$ of the hybrid. in regards to the nucleic acids of the current invention, a moderate stringency hybridization is defined as hybridization in 6×SSC, 5× Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 μg/ml denatured salmon sperm DNA at 42° C., and washed in 1×SSC and 0.5% SDS at 65° C. for 15 minutes. A very high stringency hybridization is defined as hybridization in 6× SSC, 5×Denhardt's solution, 0.5% SDS and 100 μg/ml denatured salmon sperm DNA at 42° C., and washed in 0.1×SSC and 0.5% SDS at 65° C. for 15 minutes.

II. Description

The present invention provides a transgenic woody perennial plant with altered nitrogen assimilation and/or utilization. In particular, the invention relates to altering the activity of enzymes involved in nitrogen assimilation and utilization in order to engineer trees with better growth characteristics, higher biomass production, less requirement for fertilizer, better nutritional qualities, and/or improved seed or fruit yield.

A particularly preferred embodiment of the invention, which is described in greater detail in Example 1, comprises poplar trees engineered to ectopically over-express glutamine synthetase (GS). Poplar was transformed with a heterologous GS1 (cytosolic) gene from pine. All plants regenerated in presence of the antibiotic were shown to contain the pine GS1 gene. Pine GS1 transgene expression was also detected in all selected poplar lines, and high levels of pine GS1 mRNA were shown in leaf tissues of transgenic plants. The pine GS1 polypeptide was also detected both in leaf regions enriched in photosynthetic cells (leaf blades) and in vascular elements (petioles), indicating that the gymnosperm GS1 transcripts are correctly processed by the angiosperm translational machinery. It is worthy of particular note that cytosolic GS expression in angiosperm leaves is confined to vascular elements, and therefore pine GS is ectopically expressed in poplar.

The presence of the pine GS1 polypeptide in young leaves of transgenic poplar suggests firstly that the pine GS1 protein is stable in photosynthetic cells. Moreover, ectopic expression of the pine GS1 in transgenic poplar leads to an increase in the capacity for ammonia assimilation and glutamine biosynthesis. These findings demonstrate that pine GS1 subunits are assembled in functional holoenzymes in most if not all tissues of transqenic poplar, even tissues where the endogenous cytosclic GS is not normally expressed.

The above-noted changes in GS1 expression in poplar are accompanied by modification in phenotype, including increased growth and increased leaf dimensions. The increase in GS activity in transgenic poplar leaves is positively correlated with increased protein and chlorophyll accumulation. These results show that over-expression of a cytosolic GS gene has a global effect on the synthesis of nitrogen-containing molecules and, therefore, produces a global effect on plant development.

The experimental results described hereinabove in accordance with the present invention are the first to demonstrate the increase in nitrogen-use efficiency in transgenic trees by overproducing a key enzyme involved in nitrogen metabolism. These results are surprising and unexpected, for several reasons. First, the transformation efficiency is unexpectedly high, nearly 100%, as compared with 15–20% efficiency for similar transformations reported in other woody plants. Secondly, the unusual accumulation the pine GS1 in photosynthetic tissue of poplar could not have been predicted from the normal accumulation of the endogenous angiosperm enzyme in vascular tissue only. While not limiting the mechanism of the invention in any one explanation, this unusual pine GS1 localization may be contributing to the novel phenotypic effects of the transgene as explained below.

Most significantly, however, the plant-wide improvement in growth rate and productivity observed in these trees as a result of altering the glutamine synthetase expression is surprising and unexpected. Without being limited bv any particular explanation of these results, the expression of a gymnosperm GS1-encoding gene in an angiosperm cellular environment may play a significant role in the improved nitrogen metabolism and resultant phenotypes observed. For instance, the heterologous GS1 gene or its encoded enzyme may circumvent possible down-regulatory mechanisms affecting the endogenous GS enzymes. Another possibility is that the gymnosperm enzyme may be better expressed, more stable or intrinsically more efficient than the angiosperm protein. This is likely in view of the fact that, in gymnosperms, the GS2 chloroplastic enzyme is not expressed, so the GS1 enzyme may have evolved to compensate, e.g., by higher gene expression, improved mRNA stability, improved protein stability or increased activity. The use of a transgene containing the gymnosperm GS1 enzyme in angiosperm plants represents a new a novel approach to the improvement of nitrogen metabolism.

Provided in accordance with the present invention is an expression cassette for altering the level of glutamine synthetase in plant cells. The expression cassette can be used to manipulate nitrogen metabolism in plants. In a preferred embodiment, the expression cassette comprises the coding sequence of a gymnosperm glutamine synthetase gene operably linked to a promoter. While the use of the *Pinus sylvestris* glutamine synthetase gene coding sequence is taught in Example 1, it is contemplated that any gymnosperm glutamine synthetase gene can be used to achieve similar results. In a more preferred embodiment, a *Pinus* glutamine syrthetase gene coding sequence is used. In a most preferred embodiment, a glutamine synthetase gene from *Pinus sylvestris* is used.

In another preferred embodiments, the expression cassette contains sequences that are similar to the to the pine GS1 coding sequence. Because each amino acid is encoded by several codons, a protein identical to *Pinus sylvestris* GS1 may be encoded by many different coding sequences. Additionally, proteins have a similar enzymatic function to GS1 and yet have a different amino acid sequence through the substitution of structurally similar amino acids. Therefore coding sequences that are similar yet not identical to *Pinus sylvestris* GS1 are contemplated in regards to the present invention. In a preferred embodiment, the expression vector comprises a nucleic acid sequence is at least 70% identical to Genbank Accession No. X69822 (SEQ ID NO: 3). The nucleic acid sequences are at least 80 identical in a more preferred embodiment, and at least 90% identical in a most preferred embodiment. In another embodiment, the expression cassette contains a coding sequence which encodes a protein that is at least 70% similar to the protein sequence encoded by Genbank Accession No. X69822 (SEQ ID NO: 4). The sequence encodes a amino acid sequence that is at least 80% similar in a more preferred embodiment, and at least 90% similar in a most preferred embodiment. In another embodiment, the expression cassette hybridizes to the nucleic acid in Genbank Accession No. X69822 (SEQ ID NO: 3) under conditions of moderate stringency in a preferred embodiment, high stringency in a more preferred embodiment, and very high stringency in most preferred embodiment.

Expression cassettes for expressing a DNA sequences in selected plant cells comprise a DNA sequence of interest operably linked to appropriate 5' (e.g., promoters and translational regulatory sequences) and 3' regulatory sequences (e.g., terminators). In a preferred embodiment, the coding region of a gymnosperm glutamine synthetase gene is placed under a powerful constitutive promoter, such as the Cauliflower Mosaic Virus (CaMV) 35S promoter. Other constitutive promoters contemplated for use in the present invention include, but are not limited to: figwort mosaic virus 35S promoter, T-DNA mannopine synthetase, nopaline synthase (NOS) and octopine synthase (OCS) promoters.

Expression cassettes that express a gymnosperm glutamine synthetase cene coding sequence under an inducible promoter (either its own promoter or a heterologous promoter) are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g. hydroxyproline rich cell wall protein genes), chemically-inducible gene promoters (e.g., nitrate reductase genes, gluconase genes, chitinase genes, etc.) and dark-inducible gene promoters (e.g., asparagine synthetase gene) to name a few.

Organelle-specific, tissue-specific, and development-specific promoters are also contemplated for use in the present invention. Examples of these included, but are not limited to: the ribulose bisphosphate carboxylase (RuBisCo) small subunit gene promoters or chlorophyll a/b binding protein (CAB) gene promoters for expression in photosynthetic tissue; the various seed storage protein gene promoters for expression in seeds; and the root-specific glutamine synthetase gene promoters where expression in roots is desired. Examples of organelle specific promoters include, but are not limited to the ribulose bisphosphate carboxylase (RuBisCo) large subunit gene promoter and the D1 protein promoter. In a preferred embodiment, the expression cassette comprises a chloroplast specific promoter.

Expression cassettes that down-regulate or inhibit expression of glutamine synthetase are also contemplated in accordance with the present invention. This may be necessary in order to divert nitrogen assimilation or utilization to an alternative pathway, e.g., an engineered pathway that is more efficient than the natural pathway. To accomplish this, the gymnosperm glutamine synthetase gene coding sequence or a fragment thereof may be utilized to control the production of the encoded protein. in one embodiment, full-length antisense molecules or antisense oligonucleotides, targeted to specific regions of the encoded RNA that are critical for translation, are used. The use of antisense molecules to decrease expression levels of a pre-determined gene is known in the art. In a preferred embodiment, the expression cassette expresses all or part of the antisense strand of a glutamine synthetase gene coding sequence. In another embodiment, an expression cassette that causes the over-expression of the gene targeted for down-regulation is induced to generate a co-suppression effect. In another embodiment, an expression cassette for down-regulation of the GS enzyme comprises a sequence that encodes a GS with mutations in the active site of enzyme.

In some instances, it may be advantageous to engineer the expression cassette such that it encodes a "transit" sequence enabling the encoded glutamine synthetase to cross the chloroplast membrane and localize within the chloroplast. The chloroplastic GS2 naturally comprises such a transit sequence. Cytosolic isozymes, such as GS1, can be targeted to the chloroplast through the in-frame inclusion of a DNA segment encoding such a transit sequence, according to known methods. This expression cassette may be of particular utility in production of transgenic gymnosperms having improved nitrogen metabolism, given that the gymnosperm chloroplastic GS2 is not expressed.

The coding region of the expression cassette is also operably linked to an appropriate 3' regulatory sequence. In a preferred embodiment, the nopaline synthetase polyadenylation region (NOS) is used. Other useful 3' regulatory regions include, but are not limited to the octopine (OCS) polyadenylation region.

Also provided in accordance with the present invention is a vector containing the expression cassette of the invention. This vector may be used to maintain the expression cassette in bacteria, such as *Echerichia coli*. Vectors that may be used to maintain the expression cassette in *E. coli* are well known to those in the art. The expression cassette may also have a more specialized function of introducing the expression cassette into a plant cell. These vectors may be specialized for the various well known ways of introducing transgenes into plant cells. Vectors that may be used for chloroplast transformation are contemplated in regards to the present invention. Examples of vectors for chloroplast transformation include, but are not limited to, pZS197 (Svab and Maliga, 1993, PNAS 90:915–917). In a most preferred embodiment, the vector contains the nucleic acid sequences needed to allow the expression cassette to be stably inserted into the genome of the desired woody perennial by *Agrobacterium tumefaciens*-mediated plant transformation.

In a preferred embodiment, the vector is an *Agrobacterium* binary vector. Such vectors include, but are not limited to, BIN19 (Bevan, 1984, Nucleic Acid Res 12: 8711–8721) and derivatives thereof, the pBI vector series (Jefferson et al., 1987, PNAS 83:8447–51), and binary vectors pGA482 and pGA492 (An, 1986) and others (for review, see An, 1995, Methods Mol Biol 44:47–58). In a particularly preferred embodiment, the vector is pBIN19 (Bevan, 1984, Nucleic Acid Res 12: 8711–8721).

Using an *Agrobacterium* binary vector system, the aforementioned expression cassette is linked to a nuclear drug resistance marker, such as kanamycin. In a preferred embodiment, the neomycin phosphotransferase II gene from pCaMVNEO is used (Fromm et al., 1986, Nature 319: 791–793). Other useful selectable marker systems include, but are not limited to: other genes that confer antibiotic resistances (e.g., resistance to hygromycin or bialaphos) or herbicide resistance (e.g., resistance to sulfonylurea, phosphinothricin or glyphosate). In a most preferred emnbodiment, the vector is that shown in FIG. 1.

Also provided in accordance with the present is a method to make a woody perennial plant with altered concentrations of glutamine synthetase in its cells. This method comprises the step of stably integrating the expression cassette with THE gymnosperm glutamine synthetase coding sequence into the genome of a woody perennial plant cell. Several ways to integrate a transgene such as the expression cassette into a plant cell genome are possible, including but limited to, *Agrobacterium* vectors, PEG treatment of protoplasts, biolistic DNA delivery, UV laser microbeam, gemini virus vectors, calcium phosphate treatment of protoplasts, electroporation of isolated protoplasts, agitation of cell suspensions with microbeads coated with the transforming DNA, direct DNA uptake, liposome-mediated DNA uptake and chloroplast transformation (Maliga et al., 1995, U.S. Pat. No. 5,451,513). Such methods have been published in the art. See, e.g., *Methods for Plant Molecular Biology* (Weissbach & Weissbach, eds., 1988); *Methods in Plant Molecular Biology* (Schuler & Zielinski, eds., 1989); *Plant Molecular Biology Manual* (Gelvin, Schilperoort, Verma, eds., 1993); and *Methods in Plant Molecular Biology—A Laboratory Manual* (Maliga, Klessig, Cashmore, Gruissem & Varner, eds., 1994). In a preferred embodiment, *Agrobacterium*-mediated transformation is used.

*Agrobacterium*-mediated transformation of plant nuclei is accomplished according to the following procedure:

(1) the gene is inserted into the selected *Agrobacterium* binary vector;

(2) transformation is accomplished by co-cultivation of an appropriate plant tissue (such as leaf tissue in poplar) with a suspension of recombinant *Agrobacterium*, followed by incubation (e.g., two days) on growth medium in the absence of the drug used as the selective medium (see, e.g., Horsch et al., 1985, Cold Spring Harb Symp Quant Biol 50:433–7);

(3) plant tissue is then transferred onto the selective medium to identify transformed tissue; and (4) identified transformants are regenerated to intact plants.

It should be recognized that the amount of expression, as well as the tissue specificity of expression of the transgenes in transformed plants can vary depending on the position of their insertion into the nuclear genome. Such position effects are well known in the art. For this reason, several transformants should be regenerated and tested for expression of the transgene.

Plants are transformed and thereafter screened for one or more properties, including expression of the transgene, altered nitrogen assimilation and/or utilization capacities, higher growth rates, biomass accumulation rates, higher protein or chlorophyll concentration, or changes in growth habit or appearance (e.g., alteration of phyliotaxy and canopy structure—the arrangement of leaves and branches to optimize light reception—alterations of which have been observed in the exemplified transgenic poplar).

Also provided in accordance with the present invention is woody perennial plant with altered concentrations of glutamine synthetase in its cells, which exhibits altered nitrogen metabolism. The successful transformation of poplar (an angiosperm) with a pine (a gymnosperm) GS1 gene, and the greatly improved phenotype obtained thereby, indicates that nitrogen metabolism may be improved in woody perennials more dramatically than hitherto expected. Accordingly, although in a particularly preferred embodiment the woody perennial is poplar, (specifically hybrid poplar clone INRA 7171-B4, *Populus tremula* X *P. alba*), other members of the genus *Populus* (which includes cottonwood, aspen and poplar) and the family Salicaceae are also preferred for practice of the present invention. In other embodiments, a wide variety of woody perennials are contemplated as targets for similar genetic engineering using the compositions and methods described herein. These include, but are not limited to, angiosperm forest trees, such as eucalyptus, willow (*Salix* spp.), birch, oak, cherry, maple, yellow or tulip poplar (genus *Liriodendron*), sweetgum, acacia, teak, *Liquidamber* spp. and *Alnus* spp., among others; gymnosperm forest trees, such as pine, spruce, fir, redwood, Douglas fir, *Araucaria* spp. and *Cryptomeria* spp., among others; as well as fruit and nut-bearing trees and ornamental trees and shrubs.

Also provided in accordance with the current invention is a poplar tree that has a statistically significant higher growth rate, higher protein and chlorophyll content in mature leaves, and larger nature leaf dimensions than its untransformed equivalent. In a preferred embodiment, this transgenic tree exhibits at least 10% greater growth rate during the first 3 months in the greenhouse after transformation as compared to untransformed trees of the same cultivar. More preferably, the transgenic poplar is 40% greater, and in a most preferred embodiment, the transgenic tree is 60% greater. In a more preferred embodiment, the transgenic poplar additionally has at least 10% greater grams of protein in the leaf tissue at 3 months per gram fresh weight as compared to untransformed trees of the same cultivar. More preferably, the tree exhibits at least 15% greater protein, and most preferably the tree exhibits at least 25% greater protein per gram per gram fresh weight. In a particularly preferred embodiment, the transgenic poplar additionally has at least 10% greater grams of chlorophyll per gram fresh weight in mature leaf tissue as compared to control trees of the same cultivar. In a more preferred embodiment, the trees have at least 15% greater chlorophyll, and in a most preferred embodiment, the trees have at least 20% greater chlorophyll per gram per gram fresh weight. In a more particularly preferred embodiment, the transgenic poplar additionally has at least 10% greater area per mature leaf as compared to control trees of the same cultivar. In a more preferred embodiment, the trees have at least 15% greater leaf area, and in a most preferred embodiment, the trees have at least 20% greater leaf area per leaf. In regards to the present invention, statistical significance of quantified differences is determined using one-way analysis of variance (ANOVA). This statistical test is well known to those in the art, and computer programs that carry out this test are commercially available. The level of probably (P) used is 0.05 in a preferred embodiment, 0.01 in a more preferred embodiment, and 0.001 in a most preferred embodiment.

The preceding description set forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) or Ausubel et al. (eds.) *Current Protocols in Molecular Biology*, John Wiley & Sons (1999) are used.

III. Uses for the Woody Perennials with Altered Nitrogen Metabolism

The genetically modified trees and other woody perennial plants of the present invention are expected to be of use for a variety of agronomic and/or horticultural purposes. For instance, due to their improved nitrogen metabolism, they may be productively cultivated under nitrogen nutrient deficient conditions (i.e., nitrogen-poor soils and low nitrogen fertilizer inputs) that would be detrimental to the growth of wild-type trees. The engineered trees may also be advantageously used to achieve earlier maturing, faster growing, and/or higher yielding crops and/or produce more nutritious foods (fruit and nuts) and animal fodder when cultivated under nitrogen non-limiting growth conditions (i.e. soils or media containing or receiving sufficient amounts of nitrogen nutrients to sustain healthy tree growth)

The trees and other woody plants of the present invention a so have utility as improved ornamental varieties. In addition to faster growth, these trees may have improved canopy characteristics (e.g., as results from altered phyllotaxy as discussed above), higher concentrations of pigment molecules or higher chlorophyll conents.

The trees and other woody plants of the present invention additionally have utility for forestry. Fast growing, high biomass trees have great economic value to the lumber and paper industries. The fast growing and nitrogen efficient trees of the present invention are also extremely useful for reforestation efforts, where soil nitrogen is often limiting and vigorous growth essential. Improved nitrogen assimilation also may result in higher concentrations of useful nitrogen-containing secondary compounds, such as the alkaloid quinine, or compounds involved in resistance to insects or pathogenic microorganisms.

The transgenic plants of the invention may be used for plant breeding or directly in silvaculture applications. Plants containing one transgene may be crossed with plants containing a complementary transgene in order to produce plants with enhanced or combined phenotypes.

The following example is provided to describe the invention in greater detail. It is intended to illustrate, not to limit, the invention.

EXAMPLE I

Transformation of Poplar with a Chimeric Glutamine Synthetase Gene

This example describes the transformation of poplar with a synthetic glutamine synthetase gene.

Materials and Methods

Plant materials. Hybrid poplar (*Populus tremula* X *P. alba*. clone INRA 717 1-B4) was maintained in vitro, as described (Leple et al., 1992, Plant Cell Reports 11: 137–141). Clone INRA 717 1-B4 was obtained from Dr. Lise Jouanin, Cell Biology Laboratory, INRA, Versailles, FRANCE 78026.

Gene construction. A chimeric gene composed of the cauliflower mosaic virus (CaMV) 35S promoter fused to the pine cytosolic glutamine synthetase (GS) cDNA (Canton et al., 1993, Plant Mol Biol 22: 819–828; Genbank Accession No. X69822 (SEQ ID NO: 3)) and nopaline synthetase polyadenylation region (NOS) was used to transform hybrid poplar (FIG. 1). The 1.4 kb EcoRI insert containing the full-length cytosolic GS cDNA from pGS114 (Canton et al., 1993, Plant Mol Biol 22: 819–828) was isolated and blunt ended using the Klenow fragment of DNA polymerase I. In parallel, the 1.0 kb BamHI fragment containing the neomycin phosphotransferase II (NPTII) gene from pCaMVNEO (Fromm et al., 1986, Nature 319: 791–793) was excised and the digested plasmid as blunt-ended. The 1.4 kb GS cDNA was then ligated into the digested pCaMVNEO to yield p35SGSp. The new plasmid has a 2.1 kb HindIII fragment containing the CaMV 35S-GS-NOS construct (FIG. 1). The orientation of the GS cDNA was verified by sequencing the junctions. This 2.1 kb HindIII construct was then ligated into the HindIII site of the Ti-derived disarmed binary vector pBin19 (Bevan, 1984, Nucleic Acid Res 12: 8711–8721). The new vector, pBin35SGSp, was transferred into *Agrobacterium tumefaciens* strain LBA4404 by the freeze-thaw method (Holsters et al., 1978, Mol Gen Genet 163:181–187).

Preparation of *Agrobacterium*. A single colony of *Agrobacterium tumefaciens* strain LBA4404 containing the binary piasmid vector, pBin35SGSp, as described above, was cultured in 2YT (Ausubel et al., 1987, Current Protocols in Molecular Biology. Wiley Interscience, New York) liquid medium containing antibiotics: streptomycin (200 mg L$^{-1}$) and kanamycin (50 mg L$^{-1}$). After 48 hours at 28° C. (300 rpm), the bacterial suspension was centrifuged and bacteria resuspended in liquid M1 plant cell culture medium (see below) to an OD$_{660}$ of 0.3.

Inoculation, co-cultivation, decontamination, selection, and regeneration. When in vitro grown plantlets reached a height of 5–10 cm, leaves were removed and pre-cultured in darkness for 48 hours on solidified M1 medium consisting of MS salts (Murashige and Skoog, 1962, Physiol Plant 15: 473–497), MW vitamins (Morel and Wetmore, 1951, Am J Bot 38: 141–143), 3% (w/v) sucrose, L-cysteine (1 mg L$^{-1}$) and Bacto-agar (8 g L$^{-1}$). Pretreated leaves were cut into segments 1 cm×1 cm. Leaf segments were placed directly in bacterial suspension at room temperature for 2 h then blotted onto sterile filter paper to remove excess bacteria. Explants were co-cultivated in darkness for 48 h on solidified M1 medium. For decontamination and selection for antibiotic resistance, explants were transferred to M2 medium, (consisting of M1 medium containing timentin (200 mg L$^{-1}$), kanamycin (50 mg L$^{-1}$), and 2,4-D (1 mg L$^{-1}$)) in darkness. After 4 weeks calli were separated from leaf segments and transferred to M3 medium, (consisting of M1 medium containing kanamycin (50 mg L$^{-1}$) and thidiazuron (0.1 mM)) in the light for regeneration of shoots. After shoots reached a height of 2–3 cm, they were separated and cultured on M4 medium (consisting of M1 with half-strength MS macronutrients) for root induction.

Plant culture conditions. Unless otherwise noted, in vitro cultures were maintained in a constant temperature facility at 24° C. and provided with low light (30 mmol m$^{-2}$ sec$^{-1}$; 16 h photoperiod, General Electric Cool-White fluorescent bulbs). After roots were induced, rooted shoots of transformed and control plants were transferred to a potting mix consisting of MetroMix 200 (Scotts Co., Marysville Ohio: USA). Plants were supplied with water-soluble fertilizer (20:20:20) every six weeks.

Protein extraction. Measuring from the apex, the fourth leaf of 3–4 month old greenhouse-grown plants were ground in a mortar with a pestle using glass beads (Sigma) in 50 mM Tris-HCl, 2 mM EDTA, 10 mM 2-mercaptoethanol, 10% glycerol (v/v), pH 8.0. The ratio of extraction buffer to glass beads to plant material was 3:0.5:1. Extracts were centrifuged at 22,000×g and the supernatant used for GS activity and protein determinations.

Electrophoresis and immunoblot detection of GS polypeptides. Total soluble proteins were separated by SDS-PAGE (10% acrylamide) using the discontinuous buffer system of Laemmli (Laemmli, 1970, Nature 227:680–685). Polypeptides were visualized by Coomassie-blue staining to confirm that equal amounts of protein were loaded in each lane. Proteins were electro-transferred to nylon filters and GS polypeptides were detected using polyclonal antibodies raised against the recombinant pine GS (Canton et al., 1996, FEBS Lett 393: 205–210). Protein blotting, saturation of blot, and subsequent incubations with the antiserum and washing steps were performed as described elsewhere (Gallardo et al., 1995, Planta 197: 324–332). Immunocomplexes were detected with peroxidase-conjugated immunoglobulin with a molar ratio of peroxidase to immunoglobulin of 3.3 (Vector Laboratories, Burlingame, Calif.).

Nucleic acid isolation and analysis. Genomic DNA was isolated from poplar leaves according to Dellaporta et al. (Dellaporta et al., 1993, Plant Mol Blol Rep 4:19–21). Total RNA was extracted from 5 g of leaves using the guanidine thiocyanate method as described elsewhere (Ausubel et al., 1987, Current Protocols in Molecular Biology. Wiley Interscience, New York). Southern and Northern blots were carried out followg standard procedures (Ausubel et al., 1987, supra) and hybridized with single-stranded $^{32}$P-labeled pine GS cDNA (1.4 kb) (Canton et al., 1993, Plant Mol Biol 22: 819–828), made using the randsm primer method. A mitochondrial β-ATP synthase probe from *Nicotiana plumbaginifolia* of 1.25 kb (Boutry and Chua, 1985, EMBO J 4:2159–2165) was used as control in Northern blot experiments.

For PCR amplification of genomic poplar DNA two specific primers, 5'-TGTTGATGCCATTATAAGG-CTTGTCTCTA-3' (SEQ ID NO:1) and 5'-GGTCG-TCTCAGCAATC-AT-3' (SEQ ID NO:2), were constructed, sense and antisense sequences, respectively, of the pine GS1cDNA (Canton et al., 1993, Plant Mol Biol 22: 819–828). The corresponding expected size of the amplification product was 538 bp. PCR reactions contained 1 μg of total genomic DNA, 20 pmol of each primer, 0.2 mM dNTP, 50 mM KCl, 10 mM Tris pH 8.3 and Taq DNA polymerase (Boehringer). Reaction mixtures were incubated in a thermocycler for 1 min at 92° C., followed by 30 cycles of 1 min at 91° C., 1 min at 45° C., 2 min at 72° C. and finally 5 min at 72° C. PCR amplified fragments were analyzed by using standard protocols (Ausubel et al., 1987, supra)

Results

Glutamine synthetase polypeptides in leaves of hybrid poplar. In order to determine the pattern of GS polypeptides in poplar leaves, total soluble proteins were extracted from areas enriched in photosynthetic cells (leaf tip) and areas enriched in vascular tissue (petioles). Proteins were then separated by SDS-PAGE, transferred to nitrocellulose filters, and probed with polyclonal antibodies raised against the pine glutamine synthetase (Canton et al., 1996, FEBS Lett 393: 205–210). Photosynthetic tissues display a GS polypeptide pattern enriched in the 45 kD polypeptide characteristic of the chloroplastic GS2, whereas vascular tissues (petioles) show a GS pattern characterized by the abundance of smaller, 40 kD poiypeptide subunit of the cytosolic GS1; since these tissues are not homogenous in their cell type content, the chloroplastic and cytosolic GS polypeptides are also detected as secondary bands in the protein extracts prepared from petioles and leaf tip respectively.

Gene fusions and transformation of hybrid poplar with the pine GS1. A recombinant plasmid (pBin35SGSp) containing a chimeric GS gene construct was transferred via *Agrobacterium* to leaf segments of receptor hybrid poplar plants (FIG. 1). The gene construct consisted of the 1.4 kb pine cytosolic GS cDNA (Canton et al., 1993, Plant Mol Biol 22: 819–828) under control of the cauliflower mosaic virus 35S promoter and the nos termination sequence defining a Hind III DNA-cassette of 2.1 kb (see Material and methods section). T-DNA in the plasmid binary system also contained nptII as a selectable marker. Kanamycin-resistant cultures were selected and plants regenerated using standard protocols.

Pine GS1 sequences in the genome of transformed poplar plants. To determine the presence of the GS1 transgene in the genome of kanamycin-resistant poplar plants, total DNA was isolated from leaves and two molecular approaches were conducted in parallel: Southern blotting and PCR amplification. For Southern blotting, genomic DNA from independently transformed poplar transgenic lines was digested with HindIII, restriction fragments separated on an agarose gel, and probed with radiolabeled 1.4 kb GS1 cDNA in Southern blots. A hybridization signal corresponding to the 2.1 kb HindIII-fragment of the chimeric construct (FIG. 1) was detected in all the kanamycin-resistant plants analyzed. No hybridization with labeled pine GS cDNA was detected in digests of genomic DNA of control, non-transgenic plants.

To further demonstrate the presence of pine sequences in the poplar genome, the DNA of four transforming lines was selected for PCR analysis. Specific amplification was undetectable in control plants whereas an amplification product of the expected size (538 bp) was obtained using DNA from the transformants as a template. The above data clearly indicate the presence of the introduced GS sequences in the selected transgenic clones. The copy number of the introduced gene was estimated by Southern blot analysis; four transgenic lines containing a single copy of the transgene per genome were selected for molecular and biochemical characterization.

Molecular analysis of pine GS1 expression in transgenic poplar. We next examined whether or not the introduced pine GS1 gene is expressed in transgenic poplar. Total RNA was isolated from the selected transgenic poplar and controls, separated on formaldehyde gels and blotted onto Nytran filters. Northern blots probed with radiolabeled pine GS1 cDNA revealed expression of the pine GS message in all transgenic lines. No message was detected among total RNA isolated from non-transformed controls. As an internal control, the coding sequence for the highly conserved, constitutively expressed mitochondrial β-ATP synthase gene (1.25 kb) (Boutry and Chua, 1985, EMBO J 4:2159–2165) was labelled with $^{32}$P and used as a probe. Detection of β-ATP synthase gene expression in both controls and transgenics indicates appropriate hybridization conditions and equivalent loading of RNA gels.

GS protein levels were studied to further characterize the expression of the transgene. Extracts of total proteins were prepared from whole leaves of control poplar and leaves of transgenic lines, separated on SDS-PAGE, and immunoblots developed using polyclonal antibodies raised against the recombinant pine GS1 (Canton et al., 1996, FEBS Lett 393: 205–210). In control, non-transformed leaves, the major GS polypeptide detected corresponds to the 45 kD chloroplastic GS2. However, in leaves of four independent transformed lines, a second major GS polypeptide is detected at 41 kD, which corresponds in size to the introduced pine GS1. As an additional control, total protein extracts from pine cotyledons were also assessed and showed a single GS polypeptide corresponding to the 41 kD GS1.

To confirm these data, protein extracts from tissues enriched in either photosynthetic (leaf tip) or vascular tissues (petioles) of control and transgenic poplar were subjected to western blotting analysis. It is is clear that the major GS polypeptide in vascular bundles of non-transformed poplar is the 40 kD GS1, whereas in the same tissue transgenic poplar contains the endogenous 40 kD GS1 and an additional polypeptide corresponding to the 41 kD pine cytosolic GS1 polypeptide. Moreover, in photosynthetic tissues of non-transgenic controls the major polypeptide detected is a 45 kD polypeptide corresponding to the poplar GS2, while in photosynthetic tissues of transgenic poplar lines, an additional major GS polypeptide is detected at 41 kD corresponding to the pine cytosolic GS1. These data suggest that cytosolic pine GS is expressed in both non-photosynthetic and photosynthetic poplar cells.

To confirm the ectopic expression of the cytosolic GS polypeptide in transgenic photosynthetic cells, protein was extracted from control and transgenic leaves in which midribs were removed to minimize the presence of vascular elements expressing endogenous cytosolic GS. The western blot analysis of these extracts showed that only GS2 polypeptide is detected in control plants, whereas both chloroplastic GS2 and pine cytosolic GS polypeptides are present in the extract prepared from transgenic poplar leaves.

EXAMPLE 2

Phenotypic Characterization of Transgenic Poplar

The example describes the phenotypic characteristics of poplar transformed with a synthetic glutamine synthetase gene.

Materials and Methods

The plant material. The plant material used was a hybrid poplar (*Populus tremula* X *P. alba*, clone INRA 717-1B4, Leple J C et al, 1992, Plant Cell Reports 11: 137–141). The transformation and expression of pine GS gene in transgenic poplar is described in Example 1. Regenerated plants were grown without supplemental nitrogen or other amendments.

Protein extraction. 0.4 g of leaves from each development stages of each line were ground in protein extraction buffer (50 mM Tris-HCl pH 8.0, 2 mM EDTA, 10 mM 2-mercaptoethanol, 10% glycerol (v/v)). The extracts were centrifuged at 22,000×g, and the supernatants were used for GS activity and protein content determinations.

GS activity determination. The glutathione synthetase activity was assayed by following established (Canovas et al, 1991, Planta 185: 372–378) with 3 replicates. The differences between the transgenic and non-transgenic plants were statistically analyzed with T-test. The differences between the transgenic lines were statistically analyzed with variance analysis.

Total soluble protein content determination. The protein content was determined by the method described by Bradford (1976, Anal Biochem 72: 248–254) using bovine serum albumin as standard. Three replicates were used.

Chlorophyll content determination. 0.5 g of fully-expanded leaves at each development stage of transgenic lines and controls were ground in 80% (v/v) acetone. The total chlorophyll (a+b) contents were determined by spectrophotometrically reading at the absorbance 664 nm and 647 nm (Grann and Ort, 1984, J Biol Chem 259:14003–14010). 3 replicates were used.

Height measurements. After the regenerated plants were transferred from the culture room into the greenhouse, the height growth measurements were made weekly. A total of 78 transgenic plants were measured (representing 22 independent transformation events) and 5 non-transgenic controls. The growth differences between the transgenic plants and non-trarsgenic plants were analyzed with T-test. The differences between the transgenlc lines were statistically analyzed with variance analysis.

Leaf lengths, widths, numbers, areas and total photosynthesis area measurement and calculation. The measurements of leaf length and width were made on fully-expanded mature leaves, usually to the $4^{th}$ node counting from the apex down, of the 22 transgenic lines and controls 5 months after the plants were transferred to the greenhouse. A total of 380 leaves derived from the 22 transgenic lines and 20 leaves from the control plants were measured. The leaf numbers (node numbers) were counted 2, 3 and 6 months after the plants were transferred into greenhouse. Leaf numbers of 78 transgenic plants representing 22 transgenic lines and 5 control plants were determined. Leaf area per leaf was calculated according to the length, width and shape of the leaf. The total photosynthetic area per plant was calculated according to the average area per leaf and the average leaf number per plant.

Results

GS activity, protein and chlorophyll contents. The difference in the GS activity between transgenic lines and control plants is statistically significant (Table 1). The GS activity difference among transgenic lines is also statistically significant (P<0.001). Among the transgenic lines, the highest GS activity is 50.95 nkat/gfw, and the lowest is 24.1 nkat/gfw.

The difference in the chlorophyll concentration between transgenic lines and control plants is statistically significant (Table 1). The differences in the chlorophyll contents of the transgenic lines is also statistically significant (P<0.001). The range of chlorophyll concentration of the transgenic lines is from 787.2 ug/gfw to 488.6 ug/gfw.

TABLE 1

GS activity, protein contents, and chlorophyll contents between transgenic and control poplars after 6 months in the greenhouse.

|  | GS activity (nkat/gfw) | Protein content (ug/gfw) | Chlorophyll content (ug/gfw) |
|---|---|---|---|
| Control | 22.2 | 3846.7 | 484.2 |
| Average of transgenics | 36.8 | 5132.5 | 586.1 |
| Transgenics > control | 14.6 (65.8%) | 1285.8 (33.4%) | 101.9 (21.0%) |
| P | *** | *** | *** |

***: P < 0.001
22 transgenic lines and control plants were assayed with 3 replicates.

The difference in the of soluble protein content between the transgenic lines and control plants is statistically significant (Table 1). The differences in the total soluble protein contents among transgenic lines is also statistically significant (P<0.001). Among the transgenic lines, the highest total soluble protein content is 7069.2 ug/gfw and the lowest is 3845.7 ug/gfw.

Figure 2:
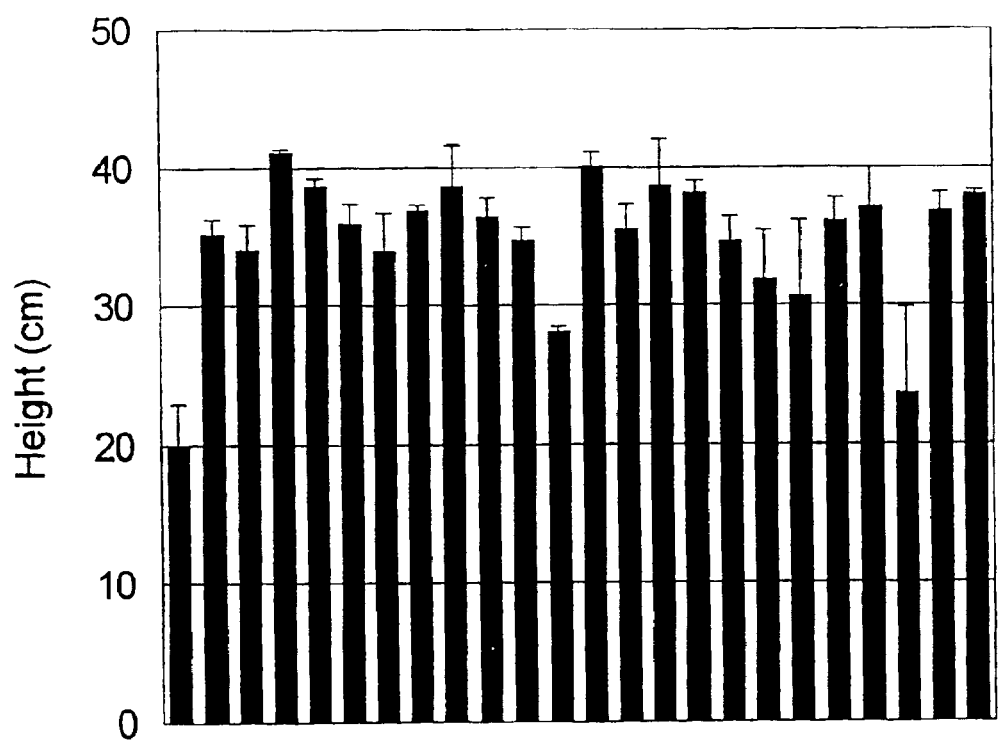
FIG. 2. The average height of controls (column 1) and transgenic trees (column 2) 2 months after the plants were moved to the greenhouse. Columns 3–24 represent the 22 transgenic lines. The height of a total of 5 controls and 78 transgenic trees were measured after 2 months in the greenhouse. The net average height of the 22 transgenic lines after 2 months in the greenhouse was 76% higher than the controls.

Height growth of transgenic and control plants. Two months after the plants transferred from the culture room to the greenhouse, the average height of the 22 transgenic lines was 76% higher than the control plants (FIG. 2). During the first 5 months in the greenhouse, all 22 transgenic lines grew taller than controls. The difference between the transgenic lines and the control plants are statistically significant (Table 2).

TABLE 2

Net Height Growth of Transgenic and Control Poplars.

| Age | | Average Height | P | Transgenics > Controls |
| --- | --- | --- | --- | --- |
| 1 Month | Transgenics | 16.4 cm | ** | 5.5 cm (50.5%) |
| | Controls | 10.9 cm | | |
| 3 Months | Transgenics | 82.7 cm | *** | 20.1 cm (32.0%) |
| | Controls | 62.7 cm | | |
| 5 Months | Transgenics | 120.2 cm | ** | 19.8 cm (19.7%) |
| | Controls | 100.4 cm | | |

*: $P < 0.001$; : $P < 0.01$
A total of 5 controls and 78 transgenic transgenic plants representing 22 transgenic lines were measured.

After the first month in the greenhouse, the heights of the transgenic plants range from 19.9 cm to 13.1 cm. The tallest transgenic line is 3.5 cm (21.3%) taller than the average height of transgenic plants, and 9.0 cm (82.6%) taller than the average height of non-transgenic control plants. After 3 months in greenhouse, the heights of the transgenic plants range from 93.3 cm to 69.0 cm. The tallest transgenic line is 10.6 cm (12.8%) taller than average height of transgenic plants, and 30.6 cm (48.8%) taller than average height of non-transgenic control plants. After 5 months in greenhouse, the tallest transgenic line is 133.2 cm, which is 13.0 cm (10.8%) taller than average height of transgenic plants, and 32.8 cm (32.7%) taller than average height of the control plants.

Figure 3:
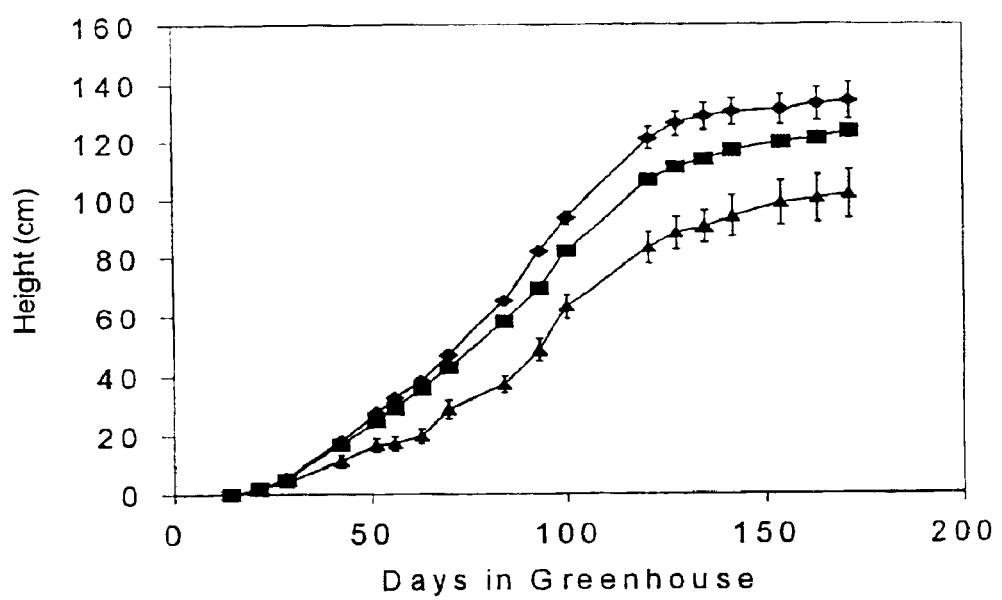
FIG. 3. Net height of control and transgenic plants during the first 6 months in greenhouse. The heights of a total of 5 controls and 78 transgenic plants were measured weekly. Square data points, average height of 22 transgenic lines; diamond data points, line 8-5, one of the fastest growth transgenic lines; and triangular data points, average height of 5 control plants.

Two weeks after the plants were transferred from culture room to greenhouse, weekly height measurements were made up to 6 months. The net growth was calculated, and graphed versus days the plants have been in greenhouse (FIG. 3). During the first 4 months, both the transgenic and control plants showed faster growth compared with growth after 4 months.

However, the transgenic plants grew faster than controls at all times during the 6 month greenhouse period.

Average leaf lengths, widths and areas of transgenic and control plants. The leaf lengths and widths were measured on 5 month old plants. The area of the leaves was calculated according to the leaf shapes. The results showed that the differences in leaf lengths, widths and areas between the transgenic and control plants are statistically significant, and the leaf areas of transgenic plants is 10.0 cm$^2$ (25.4%) larger than those of the control plants (Table 3). The area of the largest leaves from the transgenic plants is 61.2 cm$^2$, which is 46.1% larger than control plant leaves.

TABLE 3

Average leaf lengths, widths and areas per leaf of transgenic and control plants.

| | | Average | P | Transgenics > Controls |
| --- | --- | --- | --- | --- |
| Length | Transgenics | 12.2 cm | * | 1.7 cm (16.5%) |
| | Controls | 10.5 cm | | |
| Width | Transgenics | 8.6 cm | * | 0.7 cm (8.9%) |
| | Controls | 7.9 cm | | |
| Areas | Transgenics | 51.9 cm$^2$ | * | 10.0 cm$^2$ (25.4%) |
| | Controls | 41.9 cm$^2$ | | |

*: $P < 0.05$.
The measurements of leaf length and width were made on fully-expanded mature leaves of 22 transgenic lines and controls 5 months after the plants were transferred to the greenhouse. A total of 380 leaves derived from 22 transgenic lines and 20 leaves from control plants were measured.

Average leaf number per plant of transgenic and control plants. At 2, 3 and 6 months, the leaf numbers (node number) were determined. The results showed that differences in leaf number between transgenic and control plants are always statistically significant (Table 4). At 2 months, the highest leaf number in a transgenic line was 28.7 leaves per plant, 10.7 leaves (59.4%) more than the leaf number of control plants. At 3 months, the highest leaf number of a transgenic line is 38.0 leaves, which is 10.5 (38.2%) more than the leaf number of controls. At 6 months, the tallest transgenic line had 49.3 leaves per plant in average, which is 6.3 (14.7%) more than the average leaf number of the control plants.

TABLE 4

Average number of leaves per transgenic and control plants.

| | | Leaf Number | P | Transgenics > Controls |
| --- | --- | --- | --- | --- |
| 2 months | Transgenics | 25.3 | *** | 7.3 (40.6%) |
| | Controls | 18.0 | | |
| 3 months | Transgenics | 35.6 | ** | 8.1 (29.5%) |
| | Controls | 27.5 | | |
| 6 months | Transgenics | 48.0 | ** | 5.0 (11.6%) |
| | Controls | 43.0 | | |

*: $P < 0.001$; : $P < 0.01$.
The leaf numbers (node numbers) were counted 2, 3 and 6 months after plants transferred into greenhouse. The leaf numbers of 78 transgenic plants representing 22 transgenic lines and 5 control plants were counted.

Total photosynthetic areas per plant of transgenic and control plants. Six months after the plants were transferred to the greenhouse, the average photosynthetic area per plant was calculated according to the average area per leaf and the average leaf number of per plant. The results showed that the average photosynthetic area per transgenic plant and per control plant were 2491.2 cm$^2$ and 1801.2 cm$^2$, respectively. The transgenic plants have 695.5 cm$^2$ (38.3%) more photosynthetic area per plants than control plants.

The present invention is not limited to the embodiments described and exemplified above, but is capable of variation and modification without departure from the scope of the appended claims.

What is claimed is:

1. A plant expression cassette, which comprises a 5' cauliflower mosaic virus 35S promoter operably linked to a nucleic acid encoding a glutamine synthetase protein and a 3' NOS terminator sequence, wherein said nucleic acid encodes glutamine synthetase from gymnosperm *Pinus sylvestris* having the sequence of SEQ ID NO: 3, and expression of said cassette in a plant increases nitrogen metabolism in said plant.

2. A vector comprising the expression cassette of claim 1.

3. The vector of claim 2 which is an *Agrobacterium* binary vector.

4. The vector of claim 3, wherein the vector is pBIN19.

5. The vector of claim 4, which further comprises a neomycin phosphotransferase II coding sequence.

6. A method of producing a transformed Poplar plant by transforming a plant with the expression cassette of claim 1.

7. The method of claim 6, wherein the plant is the hybrid *Populus tremula* X *P. alba*.

8. The method of claim 6, wherein the transforming is by *Agrobacterium tumefaciens* mediated transformation.

9. A transgenic plant produced by the method of claim 8.

10. An isolated reproductive unit from the transgenic plant of claim 9, said unit comprising a nucleic acid encoding heterologous glutamine synthetase.

11. A transgenic cell from the transgenic plant of claim 9.

12. The transgenic plant of claim 9, which is a hybrid of *Populus tremula* X *Populus alba*.

* * * * *